United States Patent [19]

Krause et al.

[11] Patent Number: 4,648,984

[45] Date of Patent: Mar. 10, 1987

[54] NOVEL POLYGLYCOL ETHERS AND USE THEREOF

[75] Inventors: Horst-Jürgen Krause; Andreas Syldatk, both of Duesseldorf; Eric Sung, Monhein, all of Fed. Rep. of Germany

[73] Assignee: Henkel Kommanditgesellschaft auf Aktien, Duesseldorf, Fed. Rep. of Germany

[21] Appl. No.: 868,903

[22] Filed: May 29, 1986

[30] Foreign Application Priority Data

Jun. 5, 1985 [DE] Fed. Rep. of Germany ....... 3520185

[51] Int. Cl.$^4$ ................. C07C 43/164; C07C 43/178; C11D 1/72; C08G 65/34
[52] U.S. Cl. .............................. 252/174.22; 252/351; 252/DIG. 1; 568/662; 568/607
[58] Field of Search .............................. 568/662, 607; 252/174.22, 351

[56] References Cited

U.S. PATENT DOCUMENTS 2,620,360  12/1952  Britton et al. ........................ 568/607

OTHER PUBLICATIONS

Comptes Rendus, 204 (1937), pp. 1656–1658.
Journal of the American Chemical Society, 70 (1954), pp. 52–56.

Primary Examiner—Bernard Helfin
Attorney, Agent, or Firm—Ernest G. Szoke; Henry E. Millson, Jr.; Real J. Grandmaison

[57] ABSTRACT

2-benzyl-1-alkanol polyglycol ethers having the formula:

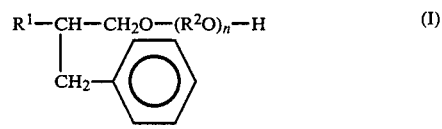

(I)

in which $R^1$ is a $C_6$ to $C_{22}$ alkyl group; $R^2$ is a $C_2$–$C_6$ alkylene group; and n is an integer from 1 to about 100.

The products are produced by heating a mixture of a ratio of an alcohol having the formula:

$$R^1-CH_2-CH_2OH$$

wherein the symbol $R^1$ has the same meaning as above with a ratio of from about 1 mole to about 10 moles, preferably 1 to 3 moles, of benzyl alcohol to a temperature of from about 180° C. to 250° C. in the presence of an alkali metal compound, and optionally a hydrogenation catalyst; separating the excess benzyl alcohol from the mixture and alkoxylating the alcohol thus obtained.

The polyglycol ether are used as wetting agents, dispersants, emulsifiers and detergents.

9 Claims, No Drawings

NOVEL POLYGLYCOL ETHERS AND USE THEREOF

BACKGROUND OF THE INVENTION

1. Field of the Invention

This invention relates to a novel class of 2-benzyl-1-alkanol polyglycol ethers. The compounds may be water-soluble or oil-soluble surface active agents and they can be used as wetting agents, dispersing agents, emulsifying agents and non-ionic cleansing agents. The compounds are especially valuable as raw materials for detergent compositions.

2. Description of the Related Art 2-benzyl-1-alkanols, and processes for their production, as well known. Their production by the mixed aldol condensation of aldehydes with benzyl alcohol, followed by hydrogenation, is described in Comptes Rendus, 204 (1937), pages 1656 to 1658. Additionally, the production of 2-benzylalkanols from benzyl alcohol and alcohols containing not more than seven carbon atoms by a Guerbet reaction is disclosed in the Journal of the American Chemical Society, 76 (1954), pages 52 to 56.

BRIEF STATEMENT OF THE INVENTION

It has been found that 2-benzyl-1-alkanol polyglycolethers having the formula

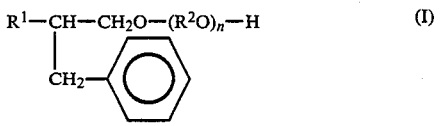

are obtained by reacting a relatively long chain alkanol with benzyl alcohol to form the corresponding 2-benzyl-1-alkanol and subsequently reacting said alkanol compound in a known manner with an alkylene oxide. The polyglycolether compounds may be water-soluble or oil-soluble, depending on the number of hydrophilizing glycolether groups, and they will exhibit outstanding activity as wetting agents, dispersants, emulsifiers and surfactants. In formula I supra, the symbol $R^1$ represents an alkyl group having from 6 to about 22 carbon atoms; $R_2$ represents an alkylene group having from 2 to about 6 carbon atoms and n represents an integer from 1 to about 100. In a preferred embodiment, the symbol $R^1$ represents an alkyl group having from about 6 to about 18 carbon atoms; $R_2$ represents an ethylene or propylene group, i.e. the symbol $(R^2-O)$ represents an ethylene glycolether group (EO) and/or a propylene glycolether group (PO). Thus, only ethylene glycolether groups or propylene glycolether groups, or mixtures of such groups in any sequence, can be present in the compounds of formula I. In a further preferred embodiment of the invention, the symbol n represents an integer of from 2 to about 50 and, in a most preferred embodiment, it represents an integer of from 3 to about 30.

The following are examples of compounds in which x and y, independently of one another, are integers of from 1 to 100 and further examples in which $x+y=n$, wherein n represents an integer from 1 to about 100, preferably from 2 to about 50 and most preferably from 3 to about 30;

2-benzyloctanol-$(EO)_x$
2-benzyldecanol-$(EO)_x$
2-benzyldodecanol-$(EO)_x$
2-benzyltetradecanol-$(EO)_x$
2-benzylhexadecanol-$(EO)_x$
2-benzyloctadecanol-$(EO)_x$
2-benzyldecanol-$(EO)_x$-$(PO)_y$
2-benzyldecanol-$(EO)_x$-$(PO)_y$
2-benzyltetradecanol-$(EO)_x$-$(PO)_y$
2-benzylhexadecanol-$(EO)_x$-$(PO)_y$
2-benzyloctanol-$(PO)_y$-$(EO)_x$
2-benzyldecanol-$(PO)_y$-$(EO)_x$
2-benzyldodecanol-$(PO)_y$-$(EO)_x$
2-benzyltetradecanol-$(PO)_y$-$(EO)_x$ In producing the 2-benzyl-1-alkanol polyglycolethers (Formula I) of this invention, a mixture of benzyl alcohol and an alkanol having the formula $$R^1-CH_2-CH_2OH \qquad \text{II}$$

is subjected to a mixed Guerbet reaction by heating said mixture to a temperature within the range of from about 150° C. to 280° C. in the presence of an alkaline-reacting alkali metal compound. In order to suppress a competing homologous Guerbet reaction of the alkanol, it is preferred to utilize an excess of benzyl alcohol in carrying out the reaction. The excess can be in a ratio of from a molar excess up to about 10 moles, and preferably from about 2 to about 3 moles, of benzyl alcohol per mole of alkanol. The alkaline-reacting catalysts which are suitable for use in this reaction include, alkali metal compounds, for example, potassium or sodium hydroxide, carbonate, borate, silicate, phosphate. Alkali metal compounds which react with the water of reaction which is formed to produce the hydroxides, for example, alcoholates, oxides, amides and hydrides. In the preferred embodiment of the invention, potassium hydroxide is employed in quantities of from about 0.1 to about 0.25 mole percent, based on the amount of alkanol used.

It has been observed that yields of considerably increased magnitude can be obtained in this reaction if hydrogenation or rather dehydrogenation catalysts are present in the reaction mixture in finely divided form. Catalysts which are suitable for use are metals of secondary groups I and VIII of the Periodic Table, such as, Cu, Fe, Ni, Co, Pt and Pd; mixed catalysts; and also salts of Fe, Zn, Co, Mn and Cr. Copper, nickel and platinum metals, and alloys thereof, have proven to be particularly suitable for use. The quantity in which these dehydrogenation catalysts are added is variable but, generally, from about 0.1% to about 5.0% by weight and preferably from about 0.2% to about 2.0% by weight, based on the reaction mixture is used.

As indicated heretofore, the Guerbet reaction is carried out at a temperature within the range of from about 150° C. to about 280° C., preferably at a temperature of from about 180° C. to about 250° C. At temperatures above the boiling point of the alcohols used, e.g., octanol boils at 194° C.; decanol boils at 229° C.; benzyl alcohol boils at 205° C., the reaction is carried out in a pressure vessel. The water which is formed during the reaction is preferably removed from the reaction mixture, for example, by distillation, with the alcohol serving as an entraining agent. Before being returned to the reaction mixture, the azeotrope which was distilled off is dehydrated. A dehydrating agent is preferably used due to the relatively small differences in density between benzyl alcohol and water. Dehydrating agents which are suitable for this purpose include, for example, salts which bind water of crystallization and also concentrated solutions of such salts, such as sodium sulfate.

Depending upon the reaction conditions employed, the 2-benzyl-1-alkanol compound is produced in the first step of the process in from about 0.5 hour to about 5 hours. At the completion of the reaction, the catalyst is removed by decantation or filtration. Any alkali remaining in solution can be neutralized before the removal of the catalyst.

In addition to unreacted starting material, particularly benzyl alcohol, the reaction mixture generally contains aliphatic Guerbet alcohols formed by the spontaneous condensation of the alkanols with one another. The 2-benzyl-1-alkanols are isolated from the reaction mixture by fractional distillation. Where it is determined that the aliphatic Guerbet alcohols will not diminish the efficacy of the 2-benzyl-1-alkanol product, and will be usable in the form of their alkoxylates, one can simply separate off the excess benzyl alcohol and other secondary products. The latter are, for the most part, alkali metal salts of acids, particularly potassium benzoate produced by the dehydrogenation of benzyl alcohol. Such salts are insoluble in the reaction mixture and they may be separated, with the catalyst, either mechanically or by washing out with water.

In the next step in the process, the 2-benzyl-1-alkanol, formed in the first step, is reacted in a known manner with an alkylene oxide, or a mixture of alkylene oxides, to produce the corresponding polyglycolethers. Alkylene oxides which are suitable for use are ethylene oxide, propylene oxide and butylene oxide and mixtures thereof. Where more than one alkylene oxide is to be employed, they may be used in any order, i.e., the 2-benzyl-1-alkanol can be reacted first with ethylene oxide and then with propylene oxide or, optionally, butylene oxide. The sequence can, of course, be reversed resulting in the production of useful products. Where more than one alkylene oxide is used, the glycolether groups are statistically distributed.

The alkoxylation of the 2-benzyl-alkanol compound is carried out at a temperature within the range of from about 60° C. to about 240° C., and preferably at a temperature within the range of from about 80° C. to about 200° C. in the presence of acidic or alkaline catalysts. The reaction is carried out perferably in a pressure vessel. Examples of acidic catalysts, which can be used are LEWIS acids, such as, boron trifluoride or aluminum chloride. It is preferred however, to use alkaline catalysts such as, the alcoholates, hydroxides, oxides, carbonates, amides and hydrides of alkali or alkaline earth metals. They are used in quantities of generally from about 0.1 to about 0.8 mole, per mole of benzylalkanol used. The alkylene oxide is introduced into the reaction mixture in gaseous form with intensive stirring. On completion of the reaction, the catalyst is inactivated by neutralization and the salt formed is mechanically separated off.

The 2-benzyl-1-alkanol polyglycolethers according to the invention are water-soluble or oil-soluble surface-active compounds, depending on the number of hydrophilizing glycolether groups. They are used as wetting agents, dispersants and emulsifiers and as nonionic surfactants. 2-Benzyl-1-alkanols containing from 8 to 20 carbon atoms and from 3 to 20 ethylene oxide groups are particularly suitable for use in detergents and cleaning preparations. Corresponding compounds containing from 5 to 30 ethylene oxide groups and, in addition, from 2 to 30 terminal propylene glycol groups are particularly distinguished by their minimal foaming. So far as their detergency is concerned, the polyglycolethers of this invention are superior to many known polyglycolethers, particularly those derived from fatty alcohols or oxo-alcohols. Their detergency is comparable to that of alkylphenol ethoxylates and, in some cases, they are superior. In contrast to the alkylphenol derivatives, the products of this invention do not form any toxic metabolites during biological degradation. The same applies to the ethoxylated aliphatic Guerbet alcohols corresponding to the following formula

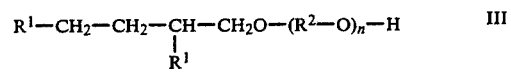

$$R^1-CH_2-CH_2-\underset{\underset{R^1}{|}}{CH}-CH_2O-(R^2-O)_n-H \qquad III$$

which accumulate as secondary products and which may optionally be present in the mixture. The symbols $R^1$, $R^2$ and n have the same meaning as in Formula I. Accordingly, the compounds corresponding to Formula I and mixtures thereof with compounds corresponding to Formula III are valuable raw materials for detergents.

For a fuller understanding of the nature and objects of this invention, reference may be had to the following examples which are furnished as further illustrations of the invention and are not to be construed in a limiting sense.

EXAMPLES

I. Preparation of the 2-benzylalkanols (A) 2-benzyl-1-dodecanol 558.9 grams (3 moles) of n-dodecanol, 642.6 grams (6 moles) of benzyl alcohol, 33.8 grams (0.525 mole) of potassium hydroxide (in the form of an 87% aqueous solution) and 12 grams of finely divided nickel (GIRDLER nickel) were heated with stirring to a temperature within the range of from about 205° C. to about 210° C. Benzyl alcohol distilling off was condensed, freed from water in a separator charged with a circulated sodium sulfate solution and returned to the reaction mixture. Thereafter, 65 ml of water in which small amounts of benzyl alcohol were dissolved were separated off in 2 hours (theoretical quantity of water of reaction 58.4 ml). After cooling, the residue consisting of catalyst and potassium benzoate was separated off and the excess benzyl alcohol was distilled off in a rotary evaporator.

The product obtained was subjected to fractional distillation in a fractionation column. The 2-benzyl-1-dodecanol boiling at 178° C. under a pressure of 0.5 mb (millibar) was isolated. The yield comprised 632 rams (74% of the theoretical). The residue and a proportion of 3% by weight in the distillate consisted of 2-decyl-1-tetradecanol.

Part of the distillate was subjected to another fractional distillation and a 2-benzyl-1-dodecanol was obtained in a purity of 99.7% (as determined by gel chromatography).

Boiling point 133° C. at 0.136 mb (0.1 Torr); reactive index $n^{20}=1.4962$ (literature value $n^{20}=1.4945$).

Elemental analysis: $C_{19}H_{32}O$ (276.5).

Hydroxyl No.: OH No.=201 (calculated 202.8).

(B) 2-benzyl-1-tetradecanol

The reaction was carried out as described in (A) using 428.8 grams (2 moles) of n-1-tetradecanol, 642.6 grams (6 moles) of benzylalcohol, 33.8 grams (0.525 mole) of potassium hydroxide (87%) and 12 grams of nickel catalyst. At a temperature within the range of from about 205° C. to about 210° C., 45 ml of water were distilled off over a period of 1.5 hours. After separation of the catalyst, the potassium benzoate and the excess benzylalcohol, 420 grams of a 92% 2-benzyl-1-tetradecanol (64% yield) were obtained by fractional distillation at 198° C./0.85 mb. The distillation residue consisted essentially of 2-dodecyl-1-hexadecanol. 2-benzyltetradecanol was obtained in a purity of 98.1% by another fractional distillation. Boiling point 181° C. at 0.68 bar (0.05 Torr), $N^{20}$=1.4935; elemental analysis: $C_{21}H_{36}O$ (304.5), OH No.=182 (calculated—184).

(C) 2-benzyl-1-octanol 911.4 grams (7 moles) of n-octanol, 1513 grams (14 moles) of benzylalcohol, 79 grams (1.225 mole) of potassium hydroxide (87%) and 24.3 grams of nickel catalyst were heated for a period of 6 hours to a temperature within the range of from about 186° C. to about 194° C. in the same way as described above. The water formed (120 ml) was distilled off together with octanol and separated off with recycling of the octanol. After cooling and separation of the catalyst, unreacted octanol and excess benzyl alcohol were distilled off and the residue fractionated. 85% by weight of the distillate, which was obtained in a quantity of 1044 grams at 116° C./0.109 mb (0.08 Torr), consisted of 2-benzyl-1-octanol and 15% by weight of 2-hexyl-1-decanol. On account of the very similar boiling points of the two alcohols, no further fractionation was undertaken. The OH No. of the mixture was 240 and the refractive index $n^{20}$ 1.4971.

(D) 2-benzyl-1-octanol and 2-benzyl-1-decanol

The starting material used was a technical mixture of n-octanol and n-decanol having a molecular weight (MW) of 141.1. 1128.8 grams (8 moles) of this mixture, together with 1729.6 grams (16 moles) of benzyl alcohol, 90.3 grams of potassium hydroxide and 28.6 grams of nickel catalyst, were heated for six hours to boiling temperature (195°–178° C.) and the water separated off from the distillate. Working up was carried out as described in C). The alcohol mixture obtained which boiled at 130° C./0.136 mb (0.1 Torr) and which still contained 15% by weight of alipatic GUERBET alcohols of octanol and decanol, had the following characteristics: OH No. 222.5, $n^{20}$=1.4963.

II. Preparation of the 2-benzyl alkanol polyglycolethers 55.3 grams (0.2 mole) of 2-benzyl-1-dodecanol and 4.43 grams of sodium methylate (100%, used as a 30% solution in methanol) were mixed and, after removal of the methanol in vacuo, were reacted while stirring in an autoclave with 74.9 grams of ethylene oxide over a period of about 1.5 hours at a temperature within the range of from about 160° C. to about 170° C. After cooling, neutralization of the catalyst with acetic acid and separation of the sodium acetate formed, a pale yellow colored product having an OH No. of 86.2 (theoretical 86.2) was obtained. The cloud point as determined in a mixture of butyl diglycol and water (in accordance with DIN 53 917, 6.2) is 68.5° C. The average degree of ethoxylation is 8.5.

The 2-benzyldodecanol polyglycolethers produced in the same way are shown in Table 1 (n=number of EO-groups; cloud point (1) according to DIN 53 917, 6.1, cloud point (2) according to DIN 53 917, 6.2):

TABLE 1

| Example No. | n | Consistency 20° C. | OH No. Found | OH No. Theor. | Cloud point °C. (1) | Cloud point °C. (2) |
|---|---|---|---|---|---|---|
| 1 | 4 | liquid | 126.8 | 123.7 | 29.5 | — |
| 2 | 6 | liquid | 103.5 | 103.7 | 53.5 | — |
| 3 | 7 | liquid | 95.2 | 96.0 | — | 66.5 |
| 4 | 8 | liquid-pasty | 88.5 | 89.2 | — | 68 |
| 5 | 8.5 | liquid-pasty | 86.2 | 86.2 | — | 68.5 |
| 6 | 9.5 | pasty | 82.2 | 83.4 | — | 70 |
| 7 | 10 | pasty | 79.8 | 78.2 | — | 70.5 |
| 8 | 11 | pasty | 76.9 | 73.9 | — | 73 |
| 9 | 13 | pasty | 67.8 | 66.1 | — | — |
| 10 | 14 | pasty | 64.3 | 62.8 | — | — |

EXAMPLE 11

In another series of tests, 89.3 grams (0.3 mole) of 97.8% 2-benzyl-1-tetradecanol were reacted as described in the previous example with 145.4 grams (3.3 moles) of ethylene oxide under pressure at a temperature within the range of from about 160° C. to about 170° C. in the presence of 7.8 grams of sodium methylate, the reaction being carried out after removal of the methanol in vacuo. On completion of the reaction (reduction in pressure), a pale yellow colored pasty product was obtained and was not purified any further. The free alkali content was 0.65%, the OH No. 74 (theoretical 71) and the cloud point in a mixture of butyl diglycol and water (DIN 53917, 6.2) 70° C. The average degree of ethoxylation was 11 EO.

EXAMPLE 12

The preparation of 2-benzyltetradecanol-13EO having an OH No. of 67.8 (theoretical 63.0) and a cloud point of 72° C. was carried out as described in Example 11.

EXAMPLES 13 TO 20

The technical 2-benzyl-1-octanol obtained in Example I, (C) containing 15% of 2-hexyl-1-decanol was reacted with ethylene oxide as described in the previous examples. The ethoxylates shown in Table 2, which are liquid at 20° C., were obtained:

TABLE 2

| Example No. | n | OH No. Found | OH No. Theor. | Cloud point °C. |
|---|---|---|---|---|
| 13 | 2 | 178 | 176 | 28 |
| 14 | 3 | 155 | 155 | 42 |
| 15 | 4 | 137 | 138 | 45 |
| 16 | 5 | 125 | 126 | 48 |
| 17 | 6 | 116 | 114 | 51 |
| 18 | 7 | 108 | 104 | 55 |
| 19 | 8 | 101 | 96 | 61 |
| 20 | 9 | 95 | 90 | 68 |

EXAMPLES 21 TO 26

The mixture of 2-benzyl-1-octanol and 2-benzyl-1-decanol obtained in Example I, (D) containing approximately 15% by weight of aliphatic GUERBET alcohols was ethoxylated in the presence of sodium methylate as described in the foregoing. The polyglycolethers obtained are shown in Table 3.

TABLE 3

| Example No. | n | OH No. Found |
|---|---|---|
| 21 | 2 | 169 |
| 22 | 3 | 150 |
| 23 | 5 | 128 |
| 24 | 6 | 113 |
| 25 | 7 | 104 |
| 26 | 9 | 94 |

III. Performance testing

The compounds of Examples 4, 5 and 17 were used as the test substances. The comparison substances used were nonylphenol reacted with 9 moles EO and a $C_{12}$-$C_{15}$ oxoalcohol reacted with 5 moles EO. The two comparison substances are commonly used surfactants having good washing properties.

(a) Foam measurements

Foaming was tested by the "perforated disc beating method" according to DIN 53902 (sheet 2) in water having a hardness of 16° dH* (160 mg CaO per liter) and a temperature of 30° C. Mixtures of 1 part by weight of the particular surfactant and 3 grams of sodium sulfate were used in increasing concentrations. The foam height (in mm) is shown in Table 4.

*dH=German hardness

TABLE 4

| Surfactant | Foam height in mm for concentrations of | | | |
|---|---|---|---|---|
| | 1.5 g/l | 2 g/l | 3 g/l | 4 g/l |
| Example 4 | 20 | 25 | 35 | 40 |
| Example 5 | 20 | 20 | 30 | 40 |
| Example 17 | 50 | 50 | 60 | 60 |
| NP 9 | 60 | 70 | 80 | 100 |
| OA 5 | 10 | 20 | 20 | 20 |

The foaming rate is the range between the two comparison substances, i.e. it is comparatively low and is not troublesome in practice.

(b) Light-duty detergency

To test detergency with respect to wool, skeins of wool yarn which had been soiled under standardized conditions were washed in a yarn washing machine at 30° C. using the same surfactant/sodium sulphate mixtures as in the foam test (test series a). The liquor ratio (yarn weight to liter washing solution) was 1:29 and the water hardness 16° dH (German hardness). After washing (washing time 15 minutes), the samples were rinsed three times with tap water and dried. The results of the photometric remission measurements are set out in Table 5.

TABLE 5

| Surfactant | Foam height in mm for concentrations of | | | |
|---|---|---|---|---|
| | 1.5 g/l | 2 g/l | 3 g/l | 4 g/l |
| Example 4 | 42.8 | 54.0 | 59.1 | 62.3 |
| Example 5 | 38.9 | 49.5 | 59.2 | 62.8 |
| Example 17 | 33.1 | 40.7 | 50.3 | 55.6 |
| NP 9 | 37.9 | 40.9 | 48.4 | 51.9 |
| OA 5 | 40.9 | 46.9 | 50.5 | 53.7 |

The surfactants according to the invention are distinguished by good to superior washing properties, particularly in the relatively high concentration range.

(c) Detergency at average to relatively high temperatures

The following tests were carried out in a Launderometer, fabric samples of cotton (Cn), refined cotton (Cnr), refined cotton/polyester blend (CnrP) and of polyester (P), which had been soiled with sebum and mineral soil, being washed under standardized conditions. The detergents used consisted of 0.75 g/l of surfactant, 1 g/l of sodium tripolyphosphate and 1 g/l of a finely crystalline, synthetic zeolite of the NaA type. The water hardness was 16° dH* and the washing temperature 90° C. for cotton and 60° C. for the other fabrics. The liquor ratio was 1:12 for cotton and 1:30 for the other fabrics. The washing drum was filled with 4.2 g of test fabric and 4.2 g of clean ballast fabric (cotton) and with 10 steel balls. The washing time was 15 mins. in each case, followed by three rinses with tapwater (16° dH). Remission was evaluated photometrically. The results are set out in Table 6 and show a distinct improvement over the comparison product, particularly in the 60° C.-washing range.

TABLE 6

| Fabric Washing Temp. | Cn 95° | Cnr 60° | CnrP 60° | P 60° |
|---|---|---|---|---|
| | % Remission | | | |
| Example 5 | 72.1 | 52.9 | 61.0 | 63.2 |
| Example 17 | 68.8 | 51.1 | 59.9 | 64.3 |
| NP 9 | 70.4 | 48.1 | 59.5 | 63.0 |

IV. Biological degradability

In the OECD screening test, the compounds prepared in accordance with Examples 1 to 26 satisfy the requirements of the Detergents Act. After 19 days, the BiAS removal was 99%.

In the closed bottle test (CB test), only 35% $BOD_{30}$/COD was initially obtained. In the Zahn-Wellens test, 87% DOC-removal and 89% COD-removal were obtained. After inoculation with cultures from the Zahn-Wellens test, 86% $BOD_{30}$/COD was obtained in the CB test also. Compared with ethoxylated nonylphenol (NP 9), there is a considerable improvement in biodegradability. In addition, aquatic toxicity is negligible compared with NP 9.

We claim:

1. 2-benzyl-1-alkanol polyglycol ethers having the formula:

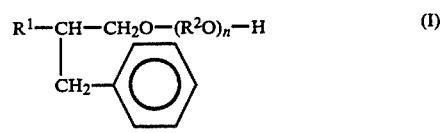

in which $R^1$ represents an alkyl group having from about 6 to about 22 carbon atoms; $R_2$ is an alkylene group having from 2 to 6 carbon atoms and n is an integer from 1 to about 100.

2. The compound of claim 1 wherein $R^1$ represents an alkyl group containing 6 to 18 carbon atom, $R^2$ is a ethylene or propylene group and n represents an integer of from about 2 to about 50.

3. The compound of claim 1 wherein $R^2$ is an ethylene group and n represents an integer of from about 3 to about 30.

4. The compound of claim 1 wherein $R^2$ is a propylene group and n is an integer of from about 3 to about 30.

5. The compound of claim 3 which is a polyglycol ether of 2-benzyl-1-dodecanol.

6. The compound of claim 3 which is a polyglycol ether of 2-benzyl-1-tetradecanol.

7. The compound of claim 3 which is a polyglycol ether of 2-benzyl-1-octanol.

8. The compound of claim 3 which is a polyglycol ether of a mixture of 2-benzyl-1-octanol and 2-benzyl-1-decanol.

9. A cleaning composition comprising a mixture of a 2-benzyl-1-alkanol polyglycolether having the formula:

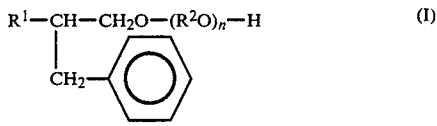

and an ethoxylated alcohol having the formula:

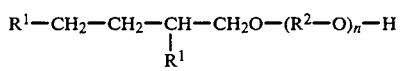

in which formula the symbol $R^1$ represents an alkyl group having from about 6 to about 22 carbon atoms; $R_2$ is an alkylene group having from 2 to 6 carbon atoms; and n is an integer from 1 to about 100.

* * * * *